United States Patent
Higson

Patent Number: 5,515,974
Date of Patent: May 14, 1996

[54] EMERGENCY AND SECURITY KIT

[76] Inventor: D. Wayne Higson, 2110 Hyde Park, Greenville, N.C. 27858

[21] Appl. No.: 370,112

[22] Filed: Jan. 9, 1995

[51] Int. Cl.⁶ .................................................. B65D 69/00
[52] U.S. Cl. .......................... 206/570; 206/576; 206/223; 206/803
[58] Field of Search ........................... 206/523, 570, 206/572, 576, 223, 803

[56] References Cited

U.S. PATENT DOCUMENTS

| | | | |
|---|---|---|---|
| 2,671,623 | 3/1954 | Toulmin, Jr ............................ | 206/803 |
| 2,982,392 | 5/1961 | Bossone ................................ | 206/803 |
| 3,254,756 | 6/1966 | Rankin ................................. | 206/803 |
| 3,371,771 | 3/1968 | Bugyi .................................. | 206/803 |
| 3,653,567 | 4/1972 | Selvaggio ............................. | 206/570 |
| 4,437,568 | 3/1984 | Hamblin .............................. | 206/223 |
| 4,763,791 | 8/1988 | Halverson et al. .................... | 206/570 |
| 4,830,579 | 5/1989 | Cheng . | |
| 4,911,296 | 3/1990 | Hart, Jr. .............................. | 206/803 |
| 5,154,600 | 10/1992 | Sylvestre ............................. | 206/803 |
| 5,156,275 | 10/1992 | Murray, Sr. . | |

*Primary Examiner*—David T. Fidei
*Attorney, Agent, or Firm*—Rhodes, Coats & Bennett

[57] ABSTRACT

The present invention relates to an emergency and security kit that includes an array of articles, such as a flashlight, first aid kit, fire extinguisher, etc., that are housed and organized within a case. In the event of an emergency or a security threat, one can open the case and gain access to one or more articles that will assist in dealing with a particular emergency or security risk.

4 Claims, 1 Drawing Sheet

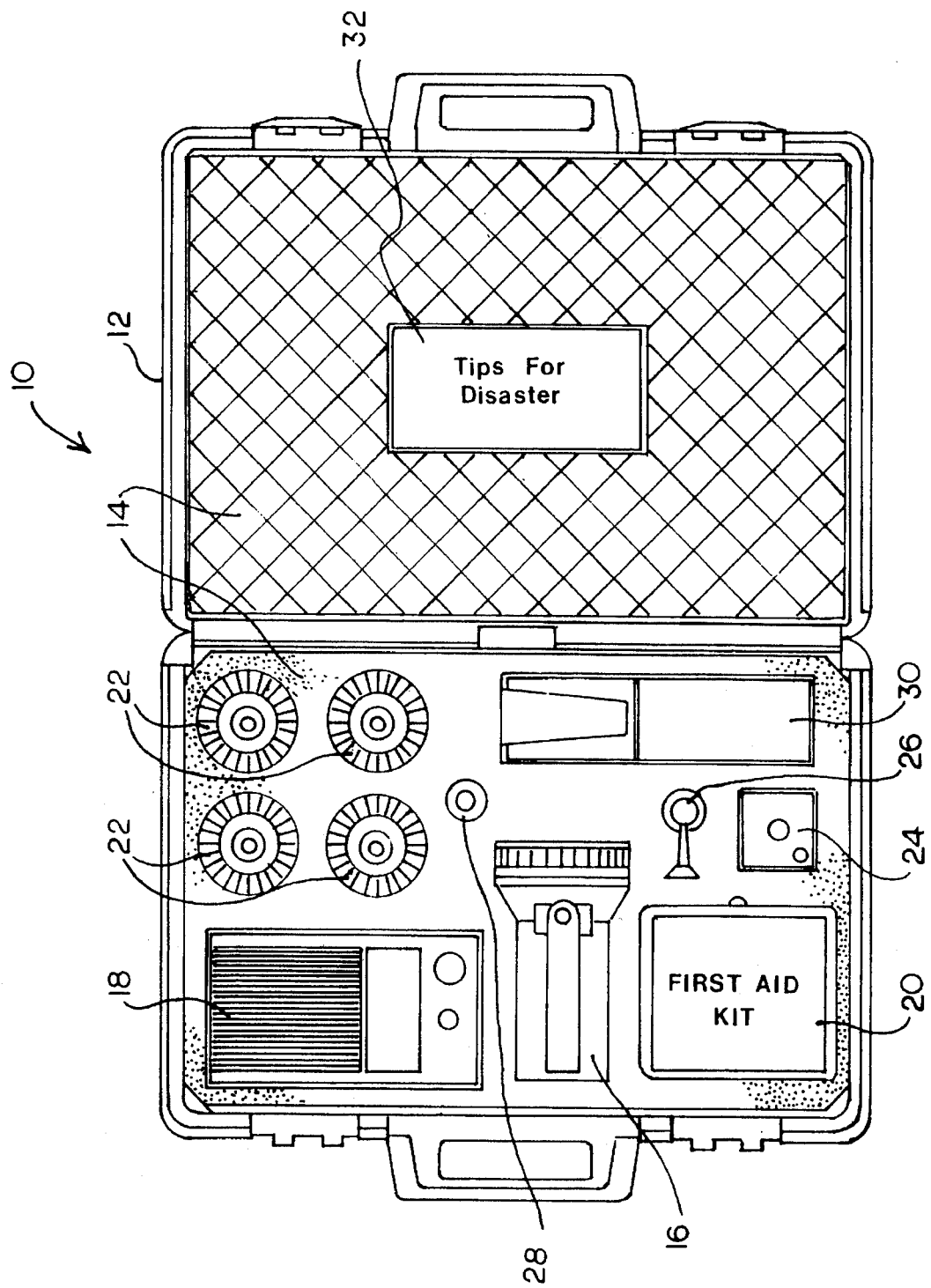

# 5,515,974

EMERGENCY AND SECURITY KIT

FIELD OF INVENTION

The present invention relates to kits and more particularly to a household emergency and security kit that includes a number of articles housed within a case wherein the articles are specifically designed to assist in dealing with an emergency or security risk situation.

BACKGROUND OF THE INVENTION

Emergency and security situations unfortunately do occur and often people find themselves unprepared to deal with such emergency and security situations. For example, many people residing in coastal areas live with the reality that from time to time, they may have to deal with the consequences of a hurricane. Others face the possibility of being subjected to tornados, floods, earthquakes, and other natural disasters. When such disasters do occur, they can be very threatening and often people that are subjected to such are not really equipped and prepared to deal with the consequences. For example, it is not unusual for there to be mass power outages as a consequence of a hurricane, flood, earthquake, or the like. For many people, when this occurs, they are unable to quickly find temporary lighting an a fire extinguisher in the case of a fire. In many cases, people may have a flashlight and/or candles, for example, but at the crucial and most threatening time may be unable to locate such in their household.

Besides having to deal with the potential problems of hurricanes, tornados, earthquakes, and the like, other people will from time to time have to deal with a serious security risk such as a prowler around the home or even a burglar. In these cases, there is often a need for a portable alarm device in order that help may be quickly summoned. In some cases, it is desirable for a person that is placed in a very threatening security situation to resort to an offensive measure such as using mace or pepper spray in order to free themself from a potentially dangerous situation.

Therefore, there has been and continues to be a need for a compact but well organized emergency and security kit that can be maintained in one's household or in any other desired location for the purpose of providing quick and easy access to articles such as flashlights, candles, a radio with a weather band and the like. As pointed out above, all too often people are confronted with emergency and security threats and while they may have articles or equipment to help them deal with such problems, they are often not easily found when the need occurs.

Thus, there is a need for a compact well-organized emergency and security kit, of a household nature, that includes an array of articles that will assist people in dealing with emergencies, natural disasters and security threats.

SUMMARY AND OBJECTS OF THE INVENTION

The present invention presents an emergency and security kit that is designed to overcome the problems discussed above and which will aid a person with coping and dealing with an emergency or security threat. In particular, the present invention entails an emergency and security kit that includes an array of articles or equipment that is designed to have utility in emergency situations and in other situations involving a threat to one's security. In this regard, the kit of the present invention includes an array of articles or equipment such as a flashlight, a series of candle lights, an alarm device such as an air horn, first aid kit, a self-contained battery, a radio with a weather band, a fire extinguisher and a spray-type security device such as pepper spray or mace.

It is therefore an object of the present invention to provide an emergency and security kit that includes an array of articles or devices that are well-organized and which are aimed at assisting a person in dealing and coping with emergency and security situations.

A further object of the present invention is to provide a kit of the character referred to above wherein there is provided an outer case for holding the various articles and an inner foam bed having cut-outs formed therein that are particularly shaped to receive certain articles that form a part of the kit.

A further object of the present invention resides in the provision of an emergency and security kit of the character discussed above which is compact, easy to handle and which can be stored in a convenient location within a house, boat, vehicle or the like.

Other objects and advantages of the present invention will become apparent and obvious from a study of the following description and the accompanying drawings which are merely illustrative of such invention.

BRIEF DESCRIPTION OF THE DRAWINGS

FIG. 1 is a top plan view of the emergency and security kit of the present invention with the case that forms a part thereof shown in an open position such that the individual articles or devices that form a part of the kit may be seen.

DETAILED DESCRIPTION OF THE INVENTION

With further reference to the drawings, the emergency and security kit of the present invention is shown therein and indicated generally by the numeral 10. Kit 10 basically comprises a case 12 that is of the type that can opened and closed. The case 12 can be hard and constructed of plastic, metal or the like. Alternatively, the case 12 can be constructed of a pliable material such as leather, vinyl or other type of pliable material. Disposed within each half of the case 12 is foam bed 14. The foam bed 14 includes a series of cavities or cut-outs that are specifically shaped to accommodate a particular article that will be housed within the case 12. As seen in the drawings, the respective articles, to be discussed subsequently herein, are designed to fit within a particular cut-out formed in the foam bed. This provides a well-organized kit and also the particularly shaped cut-outs tend to hold and secure the respective kit articles in place.

Now, turning to the articles or devices stored within the case 12, it is seen that the kit 10 of the present invention is designed to include a flashlight 16. In addition, there is provided an AM/FM radio 18 that is preferably provided with a weather band. This is of significant utility in cases of hurricanes, tornados, floods and the like. Disposed next to the flashlight 16 is a first aid kit 20.

Also provided as a part of kit 10 is a series of candle lights 22. In the embodiment illustrated, the candle lights 22 could be of various candle type designs but in the case of the embodiment illustrated herein, the candle lights are of the emergency Code 1 type. Also provided with the kit 10 is an auxiliary battery 24 that could be of any suitable voltage or amperage type. For example, battery 24 could be of a 6-volt type which would be suitable for powering, in the way of an example, a lantern. It is understood that other devices such as flares, whistles, and the like could be included in the kit.

For security purposes, the kit 10 is provided with an alarm device that is in the form of an air horn 26. In addition, there is provided a security spray 28 such as a pepper spray or mace. Also, kit 10 is provided with a fire extinguisher 30.

Finally, provided with the kit 10 is a booklet or other form of written material that is designed to impart valuable information to a person with respect to disasters such as hurricanes, tornados, earthquakes, floods, etc. In addition, the booklet or leaflet 32 can provide information on a wide variety of subjects relating to security and emergency situations.

The articles provided herein with the kit 10 are selected and provided for so as to cover a relatively wide range of emergency and security needs. It will be understood that other specific articles or devices of the basic type disclosed herein can be provided with the kit 10 of the present invention.

One of the principal advantages of the emergency and security kit 10 of the present invention is that the various devices and articles included within the kit are well-organized and are presented in a form that can be easily stored and maintained in a household, vehicle, boat, or any other location that might lend itself to emergency and security needs from time to time. Thus, when there is an occasion for the need of a flashlight or a fire extinguisher, a person having access to the kit 10 of the present invention can easily and immediately gain access to the same and can quickly and easily retrieve a selected device so that he or she may deal with a particular emergency or security situation at hand. Thus, the individual does not waste valuable time attempting to find a flashlight, fire extinguisher or the like that may be stored in any number of locations within a household for example. Once the emergency and security kit 10 of the present invention is retrieved, then the various articles or devices that comprise the same are easily viewed and a quick selection of the appropriate article or device can be made.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced therein.

What is claimed is:

1. A multi-purpose emergency and security household kit that includes an army of articles that may assist one in dealing with a wide range of emergency and security situations, comprising in combination: a case for holding a series of emergency and security articles; an inner foam bed disposed interiorly of the case for holding and organizing the respective emergency and security articles housed within the case; a series of cut-outs formed in the inner foam bed for receiving and holding the various emergency and security articles and wherein each respective cut-out is particularly shaped to receive an emergency and security article; and wherein the emergency and security articles disposed within the case include a flashlight, at least one candle-type lighting device, a first aid kit, a fire extinguisher, a radio, an alarm device, a security type spray, and a written booklet disclosing information relative to disasters such as hurricanes and tornadoes.

2. The emergency and security household kit of claim 1 wherein the kit further includes a self-contained batteries.

3. The multi-purpose emergency and security household kit of claim 1 wherein the kit consists essentially of the structure and articles set forth in claim 1.

4. The emergency and security household kit of claim 1 wherein the kit consists of the emergency and security articles recited.

* * * * *